(12) United States Patent
Al Maharmeh et al.

(10) Patent No.: US 11,051,747 B2
(45) Date of Patent: Jul. 6, 2021

(54) ELECTROCARDIAGRAM (ECG) PROCESSOR

(71) Applicant: Khalifa University of Science and Technology, Abu Dhabi (AE)

(72) Inventors: Hamza Yacoub Al Maharmeh, Sharjah (AE); Hani Hasan Mustafa Saleh, Round Rock, TX (US); Baker Mohammad, Austin, TX (US); Mohammed Ismail Elnaggar, Abu Dhabi (AE); Mahmoud Al-Qutayri, Manchester (GB)

(73) Assignee: Khalifa University of Science and Technology, Abu Dhabi (AE)

( * ) Notice: Subject to any disclaimer, the term of this patent is extended or adjusted under 35 U.S.C. 154(b) by 682 days.

(21) Appl. No.: 15/716,964

(22) Filed: Sep. 27, 2017

(65) Prior Publication Data

US 2019/0090773 A1    Mar. 28, 2019

(51) Int. Cl.
*A61B 5/364*    (2021.01)
*A61B 5/00*    (2006.01)
(Continued)

(52) U.S. Cl.
CPC .............. *A61B 5/364* (2021.01); *A61B 5/316* (2021.01); *A61B 5/7278* (2013.01);
(Continued)

(58) Field of Classification Search
CPC . A61B 5/0468; A61B 5/04012; A61B 5/7278; A61B 5/02405; A61B 5/0245; A61B 5/0428
See application file for complete search history.

(56) References Cited

U.S. PATENT DOCUMENTS 4,700,712 A * 10/1987 Schmid .................. A61B 5/044
600/512
5,277,189 A    1/1994 Jacobs
(Continued)

OTHER PUBLICATIONS

Alonso-Atienza, Felipe et al., "Detection of Life-Threatening Arrhythmias Using Feature Selection and Support Vector Machines," IEEE Transactions on Biomedical Engineering, vol. 61, No. 3, Mar. 2014, pp. 832-840.
(Continued)

*Primary Examiner* — Catherine M Voorhees
*Assistant Examiner* — Roland Dinga
(74) *Attorney, Agent, or Firm* — Withrow & Terranova, P.L.L.C.

(57) ABSTRACT

An electrocardiogram (ECG) processor is disclosed. The ECG processor includes ECG sampling circuitry configured in a first mode to acquire a continuous ECG sample set from an ECG signal by digitally sampling the ECG signal at a Nyquist rate for a first predetermined number of heartbeats and in a second mode to acquire a non-continuous ECG sample set from the ECG signal for a second predetermined number of heartbeats by digitally sampling active regions of the ECG signal that contain a PQRST complex and not from silent regions between adjacent PQRST complexes. The ECG processor also includes processing circuitry configured to determine from the continuous ECG sample set relative locations of the active regions and provide the relative locations of the active regions to the ECG sampling circuitry for sampling the ECG signal in the second mode.

19 Claims, 4 Drawing Sheets

(51) Int. Cl.
*A61B 5/316* (2021.01)
*A61B 5/0245* (2006.01)
*A61B 5/024* (2006.01)
*A61B 5/30* (2021.01)

(52) U.S. Cl.
CPC ......... *A61B 5/0245* (2013.01); *A61B 5/02405* (2013.01); *A61B 5/30* (2021.01)

(56) References Cited

U.S. PATENT DOCUMENTS

| | | | |
|---|---|---|---|
| 5,758,654 | A | 6/1998 | Burton-Krahn et al. |
| 7,155,282 | B1 | 12/2006 | Min et al. |
| 7,610,086 | B1 | 10/2009 | Ke et al. |
| 9,717,438 | B2 | 8/2017 | Bayasi et al. |
| 2005/0004481 | A1 | 1/2005 | Xue et al. |
| 2005/0234361 | A1* | 10/2005 | Holland ............... A61B 5/0452 600/510 |
| 2006/0116733 | A1 | 6/2006 | Gunderson |
| 2007/0203418 | A1 | 8/2007 | Starc |
| 2007/0276274 | A1 | 11/2007 | Kawada et al. |
| 2008/0194978 | A1* | 8/2008 | Beker ................ A61B 5/0452 600/516 |
| 2008/0300497 | A1 | 12/2008 | Krause et al. |
| 2010/0217144 | A1 | 8/2010 | Brian |
| 2012/0123232 | A1* | 5/2012 | Najarian ............... A61B 5/0022 600/345 |
| 2012/0257698 | A1* | 10/2012 | Zhang ................. H03M 1/1265 375/355 |
| 2013/0317380 | A1* | 11/2013 | Liley ..................... A61B 5/0476 600/544 |
| 2015/0032990 | A1 | 1/2015 | Markovic et al. |
| 2015/0141857 | A1* | 5/2015 | Nallathambi ........ A61B 5/0452 600/509 |
| 2016/0120430 | A1 | 5/2016 | Bayasi et al. |
| 2016/0120431 | A1 | 5/2016 | Habte et al. |
| 2016/0135705 | A1* | 5/2016 | Liu ..................... A61B 5/04012 600/509 |
| 2016/0374578 | A1* | 12/2016 | Kacelenga ........... A61B 5/0404 600/483 |
| 2017/0095175 | A1 | 4/2017 | Allavatam |
| 2017/0265768 | A1 | 9/2017 | Bayasi et al. |
| 2020/0085330 | A1* | 3/2020 | Di Poian .............. A61B 5/7232 |

OTHER PUBLICATIONS

Amann, Anton et al., "Detecting Ventricular Fibrillation by Time-Delay Methods," IEEE Transactions on Biomedical Engineering, vol. 54, No. 1, Jan. 2007, pp. 174-177.

Andreão, Rodrigo V. et al., "ECG Signal Analysis Through Hidden Markov Models," IEEE Transactions on Biomedical Engineering, vol. 53, No. 8, Aug. 2006, pp. 1541-1549.

Author Unknown, "American Heart Association," American Heart Association, Inc., 2016, Accessed: Apr. 19, 2016, 3 pages, Available at: http://www.heart.org/HEARTORG/.

Author Unknown, "Recommendations for measurement standard in quantitative electrocardiography," European Heart Journal: The CSE Working Party, vol. 6, No. 10, Oct. 1985, pp. 815-825.

Banerjee, Swati et al., "Application of Cross Wavelet Transform for ECG Pattern Analysis and Classification," IEEE Transactions on Instrumentation and Measurement, vol. 63, No. 2, Feb. 2014, pp. 326-333.

Barro, S. et al., "Algorithmic sequential decision-making in the frequency domain for life threatening ventricular arrhythmias and imitative artefacts: a diagnostic system," Journal of Biomedical Engineering, vol. 11, No. 4, Jul. 1989, pp. 320-328.

Bayasi, Nourhan et al., "A 65-nm Low Power ECG Feature Extraction System," 2015 IEEE International Symposium on Circuits and Systems (ISCAS), May 2015, IEEE, pp. 746-749.

Bayasi, Nourhan et al., "Adaptive Technique for P and T Wave Delineation in Electrocardiogram Signals," 2014 36th Annual Conference of the IEEE Engineering in Medicine and Biology Society (EMBC), Aug. 26-30, 2014, Chicago, IL, pp. 90-93.

Bayasi, Nourhan et al., "Detection of Ventricular Arrhythmia Based on Unique ECG Parameters and Linear Discriminant Analysis," IEEE Transactions on Biomedical Engineering, 2014, 10 pages.

Bayasi, Nourhan et al., "Low-Power ECG-Based Processor for Predicting Ventricular Arrhythmia," IEEE Transactions on Very Large Scale Integration (VLSI) Systems, vol. 24, No. 5, May 2016, pp. 1962-1974.

Clifford, Gari D., "Chapter 3: ECG Statistics, Noise, Artifacts, and Missing Data," Advanced Methods and Tools for ECG Data Analysis, Artech House, 2006, pp. 55-99.

Coast, Douglas A. et al., "QRS Detection Based on Hidden Markov Modeling," ECG Signal Processing II, 1989, IEEE, 2 pages.

Da Poian, G., et al., "Energy and Quality Evaluation for Compressive Sensing of Fetal Electrocardiogram Signals," Sensors 2017, vol. 17, No. 9, Dec. 22, 2016, 13 pages.

De Azevedo Botter, Eduardo et al., "A Neural Network With Asymmetric Basis Functions for Feature Extraction of ECG P Waves," IEEE Transactions on Neural Networks, vol. 12, No. 5, Sep. 2001, pp. 1252-1255.

De Chazal, Philip et al., "Automatic Classification of Heartbeats Using ECG Morphology and Heartbeat Interval Features," IEEE Transactions on Biomedical Engineering, vol. 51, No. 7, Jul. 2004, pp. 1196-1206.

Dumont J. et al., "Parameter Optimization of a Wavelet-Based Electrocardiogram Delineator with an Evolutionary Algorithm," Computers in Cardiology, vol. 32, Sep. 2005, IEEE, pp. 707-710.

Elgendi, Mohamed et al., "Recognition of T Waves in ECG signals," 2009 IEEE 35th Annual Northeast Bioengineering Conference, Apr. 3-5, 2009, Boston, MA, 2 pages.

Fisher, R. A., "The Use of Multiple Measurements in Taxonomic Problems," Annals of Eugenics, vol. 7, No. 2, 1936, pp. 179-188.

Goldberger, Ary L. et al., "PhysioBank, PhysioToolkit, and PhysioNet: Components of a New Research Resource for Complex Physiologic Signals," Circulation, vol. 101, No. 2, Jun. 13, 2000, 7 pages.

Golpayegani, Glayol Nazari et al., "A novel approach in ECG beat recognition using adaptive neural fuzzy filter," Journal of Biomedical Science and Engineering, vol. 2, 2009, pp. 80-85.

Hamilton, Patrick S. et al., "Quantitative Investigation of QRS Detection Rules Using the MIT/BIH Arrhythmia Database," IEEE Transactions on Biomedical Engineering, vol. BME-33, No. 12, Dec. 1986, pp. 1157-1165.

Homaeinezhad, M.R. et al., "ECG arrhythmia recognition via a neuro-SVM-KNN hybrid classifier with virtual QRS image-based geometrical features," Expert Systems with Applications, vol. 39, 2012, pp. 2047-2058.

Jekova, Irena, "Shock advisory tool: Detection of life-threatening cardiac arrhythmias and shock success prediction by means of a common parameter set," Biomedical Signal Processing and Control, vol. 2, No. 1, 2007, pp. 25-33.

Khawaja, Antoun, "Automatic ECG Analysis Using Principal Component Analysis and Wavelet Transformation," Karlsruhe Transactions on Biomedical Engineering, vol. 3, Univ.-Verlag Karlsruhe, 2007, 234 pages.

Khushaba, Rami N. el al., "Driver Drowsiness Classification Using Fuzzy Wavelet-Packet-Based Feature-Extraction Algorithm," IEEE Transactions on Biomedical Engineering, vol. 58, No. 1, Jan. 2011, pp. 121-131.

Kligfield, Paul, "The Centennial of the Einthoven Electrocardiogram," Journal of Electrocardiography, vol. 35, No. 4, Part B, Oct. 2002, pp. 123-129.

Laguna, P. et al., "A Database for Evaluation of Algorithms for Measurement of QT and Other Waveform Intervals in be ECG," Computers in Cardiology, vol. 24, 1997, pp. 673-676.

Li, Cuiwei et al., "Detection of ECG Characteristic Points Using Wavelet Transforms," IEEE Transactions on Biomedical Engineering, vol. 42, No. 1, Jan. 1995, pp. 21-28.

Li, Qiao et al., "Ventricular Fibrillation and Tachycardia Classification Using a Machine Learning Approach," IEEE Transactions on Biomedical Engineering, vol. 61, No. 6, Jun. 2014, pp. 1607-1613.

(56) References Cited

OTHER PUBLICATIONS

Lin, Chao et al., "P- and T-Wave Delineation in ECG Signals Using a Bayesian Approach and a Partially Collapsed Gibbs Sampler," IEEE Transactions on Biomedical Engineering, vol. 57, No. 12, Dec. 2010, pp. 2840-2849.
Mallat, Stéphane, "A Wavelet Tour of Signal Processing," Academic Press, Second Edition, 1999, pp. 1-109.
Martínez, Juan Pablo et al., "A Wavelet-Based ECG Delineator: Evaluation on Standard Databases," IEEE on Biomedical Engineering, vol. 51, No. 4, Apr. 2004, pp. 570-581.
Mazomenos, E. B. et al., "A Time-Domain Morphology and Gradient based Algorithm for ECG Feature Extraction," 2012 IEEE International Conference on Industrial Technology (ICIT), Mar. 19-21, 2012, Athens, pp. 117-122.
Mazomenos, Evangelos B. et al., "A Low-Complexity ECG Feature Extraction Algorithm for Mobile Healthcare Applications," IEEE Journal of Biomedical and Health Informatics, vol. 17, No. 2, Mar. 2013, pp. 459-469.
Mehta, S. S. et al., "Detection of QRS complexes in electrocardiogram using support vector machine," Journal of Medical Engineering and Technology, vol. 32, No. 3, May/Jun. 2008, pp. 206-215.
Mehta, S. S. et al., "Recognition of P and T waves in Electrocardiograms Using Fuzzy Theory," Proceedings of the First Regional Conference IEEE Engineering in Medicine and Biology Society and 14th Conference of the Biomedical Engineering Society of India, An International Meeting, Feb. 15-18, 1995, New Delhi, pp. 2.54-2.55.
Mishra, A., et al., "ECG Signal Compression Using Compressive Sensing and Wavelet Transform," 34th Annual International Conference of the IEEE Engineering in Medicine and Biology Society, Aug. 28-Sep. 1, 2012, California, USA, 4 pages.
Murthy, I. S. N. et al., "Analysis of ECG from Pole-Zero Models," IEEE Transactions on Biomedical Engineering, vol. 39, No. 7, Jul. 1992, pp. 741-751.
Niknazar, Mohammad et al., "Fetal ECG Extraction by Extended State Kalman Filtering Based on Single-Channel Recordings," IEEE Transactions on Biomedical Engineering, vol. 60, No. 5, 2013, pp. 1345-1352.
Oweis, Rami J. et al., "Seizure classification in EEG signals utilizing Hilbert-Huang transform," Biomedical Engineering Online, vol. 10, No. 38, 2011, 15 pages.
Pal, Saurabh et al., "Empirical mode decomposition based ECG enhancement and QRS detection," Computers in Biology and Medicine, vol. 42, No. 1, Jan. 2012, pp. 83-92.
Pan, Jiapu et al., "A Real-Time QRS Detection Algorithm," IEEE Transactions on Biomedical Engineering, vol. BME-32, No. 3, Mar. 1985, pp. 230-236.
Pardey, J., "Detection of Ventricular Fibrillation by Sequential Hypothesis Testing of Binary Sequences," Computers in Cardiology, vol. 34, 2007, pp. 573-576.
Phyu, Myint Wai et al., "A Real-Time ECG QRS Detection ASIC Based on Wavelet Multiscale Analysis," IEEE Asian Solid-State Circuits Conference, 2009, A-SSCC 2009, Nov. 16-18, 2009, Taipei, Taiwan, pp. 293-296.
Polania, L. F., et al, "Compressed Sensing Based Method For ECG Compression," 2011 IEEE International Conference on Acoustics, Speech and Signal Processing (ICASSP), May 22-27, 2011, 4 pages.
Sayadi, Omid et al., "Robust Detection of Premature Ventricular Contractions Using a Wave-Based Bayesian Framework," IEEE Transactions on Biomedical Engineering, vol. 57, No. 2, Feb. 2010, pp. 353-362.
Schleifer, J. William et al., "Ventricular Arrhythmias: State of the Art," Cardiology Clinics, vol. 31, No. 4, 2013, pp. 595-605.
Singh, Yogendra Narain et al., "ECG to Individual Identification," 2nd IEEE International Conference on Biometrics: Theory, Applications and Systems, 2008, BTAS 2008, Sep. 29-Oct. 1, 2008, Arlington, VA, 8 pages.

Sun, Yan et al., "Characteristic wave detection in ECG signal using morphological transform," BMC Cardiovascular Disorders, vol. 5, No. 28, 2005, 7 pages.
Non-Final Office Action for U.S. Appl. No. 15/616,069, dated Mar. 29, 2019, 11 pages.
Tan, K. F. et al., "Detection of the QRS Complex, P Wave and T Wave in Electrocardiogram," First International Conference on Advances in Medical Signal and Information Processing, 2000, Bristol, pp. 41-47.
Tawfic, I., et al., "Compressed Sensing Of ECG Signal For Wireless System With New Fast Iterative Method," Computer Methods and Programs in Biomedicine, vol. 122, No. 3, Dec. 2015, 13 pages.
Tekeste, Temesghen et al., "A Biomedical SoC Architecture for Predicting Ventricular Arrhythmia," IEEE International Symposium on Circuits and Systems (ISCAS), May 22-25, 2016, Montreal, QC, IEEE, pp. 2262-2265.
Tekeste, Temesghen et al., "Adaptive ECG Interval Extraction," 2015 IEEE International Symposium on Circuits and Systems (ISCAS), May 24-27, 2015, IEEE, pp. 998-1001.
Yu, W., et al., "Adaptive compressive engine for real-time electrocardiogram monitoring under unreliable wireless channels," IET Communications, vol. 10, No. 6, Apr. 14, 2016, 9 pages.
Zhang, H., et al., "Implementation Of Compressive Sensing In ECG And EEG Signal Processing," The Journal of China Universities of Posts and Telecommunications, vol. 17, No. 6, Dec. 2010, 5 pages.
Zhang, Xu-Sheng et al., "Detecting Ventricular Tachycardia and Fibrillation by Complexity Measure," IEEE Transactions on Biomedical Engineering, vol. 46, No. 5, 1999, pp. 548-555.
Zhou, J., et al., "Asynchronous Binary Compressive Sensing for Wireless Body Sensor Networks," 2013 IEEE 9th International Conference on Mobile Ad-hoc and Sensor Networks, Dec. 11-13, 2013, 6 pages.
Zong, W. et al., "A QT Interval Detection Algorithm Based on ECG Curve Length Transform," Computers in Cardiology, vol. 33, Oct. 2006, IEEE, pp. 377-380.
Zong, W. et al., "A Robust Open-source Algorithm to Detect Onset and Duration of QRS Complexes," Computers in Cardiology, vol. 30, 2003, pp. 737-740.
Zong, W. et al., "Automated ECG Rhythm Analysis Using Fuzzy Reasoning," Computers in Cardiology, vol. 25, 1998, pp. 69-72.
Non-Final Office Action for U.S. Appl. No. 14/926,483, dated Sep. 28, 2016, 8 pages.
Final Office Action for U.S. Appl. No. 14/926,483, dated Jan. 20, 2017, 7 pages.
Notice of Allowance for U.S. Appl. No. 14/926,483, dated Mar. 24, 2017, 11 pages.
Corrected Notice of Allowance for U.S. Appl. No. 14/926,483, dated Apr. 28, 2017, 4 pages.
Non-Final Office Action for U.S. Appl. No. 14/926,554, dated Sep. 28, 2016, 14 pages.
Final Office Action for U.S. Appl. No. 14/926,554, dated Jan. 26, 2017, 11 pages.
Advisory Action for U.S. Appl. No. 14/926,554, dated Apr. 3, 2017, 3 pages.
Non-Final Office Action for U.S. Appl. No. 14/926,554, dated Jun. 15, 2017, 12 pages.
Final Office Action for U.S. Appl. No. 14/926,554, dated Sep. 27, 2017, 12 pages.
Advisory Action for U.S. Appl. No. 14/926,554, dated Jan. 4, 2018, 3 pages.
Non-Final Office Action for U.S. Appl. No. 14/926,554, dated Apr. 3, 2018, 12 pages.
Final Office Action for U.S. Appl. No. 15/616,069, dated Jul. 3, 2019, 10 pages.
Notice of Allowance for U.S. Appl. No. 15/616,069, dated Sep. 11, 2019, 8 pages.

* cited by examiner

ELECTROCARDIAGRAM (ECG) PROCESSOR

GOVERNMENT SUPPORT

This invention was made with government funds under contract number 2013-HJ-2440 awarded by the ATIC-SRC Center for Energy Efficient Electronic Systems. The U.S. Government may have rights in this invention.

RELATED APPLICATIONS

This application is related to U.S. Pat. No. 9,717,438, issued Aug. 1, 2017, and titled MEDICAL DEVICE FOR DETECTING A VENTRICULAR ARRHYTHMIA EVENT; U.S. patent application Ser. No. 15/616,069, filed Jun. 7, 2017, now U.S. Pat. No. 10,548,499, and titled MEDICAL DEVICE AND METHOD FOR DETECTING A VENTRICULAR ARRHYTHMIA EVENT; and U.S. patent application Ser. No. 14/926,554, filed Oct. 29, 2015, now U.S. Pat. No. 10,194,821, and titled MEDICAL DEVICE HAVING AUTOMATED ECG FEATURE EXTRACTION, the disclosures of which are hereby incorporated herein by reference in their entireties.

FIELD OF THE DISCLOSURE

The present disclosure relates to biomedical devices and methods usable to monitor electrocardiogram signals.

BACKGROUND

The electrical activity of the heart is presented by the surface electrocardiogram (ECG) signal. Due to ease of use and non-invasiveness, the ECG is used as a prime tool not only to monitor the functionality of the heart but also to diagnose cardiac arrhythmia by extracting information about intervals, amplitudes, and wave morphologies such as P, QRS, and T-waves. Extracted features from the ECG signal play an essential role in diagnosing many cardiac diseases. Moreover, medical devices have been developed that are wearable by patients or are implantable in patients to automatically monitor the ECG signal and take a predetermined action. For example, a wearable medical device may interface with a smartphone to remotely report an abnormal ECG to a medical professional, and an implantable medical device may be configured to apply a shock treatment to the patient's heart if an arrhythmia is detected. Both wearable and implantable medical devices are battery powered. Therefore, a critical requirement for both wearable and implantable medical devices is energy efficiency, which in part is related to data collection and storage efficiency. Traditional wearable and implantable medical devices that monitor the ECG signal from a patient's heart completely digitize the ECG signal while using data compression techniques. However, because regions within the ECG signal of no diagnostic value are processed during each heartbeat, these traditional wearable and implantable medical devices provide less overall energy efficiency than desired. Thus, an implantable medical device and method that provides greater energy efficiency while processing an ECG signal is needed.

SUMMARY

An electrocardiogram (ECG) processor is disclosed. The ECG processor includes ECG sampling circuitry configured in a first mode to acquire a continuous ECG sample set from an ECG signal by digitally sampling the ECG signal at a Nyquist rate for a first predetermined number of heartbeats and in a second mode to acquire a non-continuous ECG sample set from the ECG signal for a second predetermined number of heartbeats by digitally sampling active regions of the ECG signal that contain a PQRST complex and not from silent regions between adjacent PQRST complexes. The ECG processor also includes processing circuitry configured to determine from the continuous ECG sample set relative locations of the active regions and provide the relative locations of the active regions to the ECG sampling circuitry for sampling the ECG signal in the second mode.

In some exemplary embodiments, the ECG processor further includes a memory configured to store the non-continuous ECG sample set. Moreover, some exemplary embodiments include an active regions reconstruction circuitry implementation of the smoothed L0 algorithm to reconstruct the ECG signal from the non-continuous ECG sample set. Yet other exemplary embodiments include firmware that when invoked performs the smoothed L0 algorithm to generate data from the non-continuous ECG sample set for reconstruction of the ECG signal.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure and, together with the description, serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
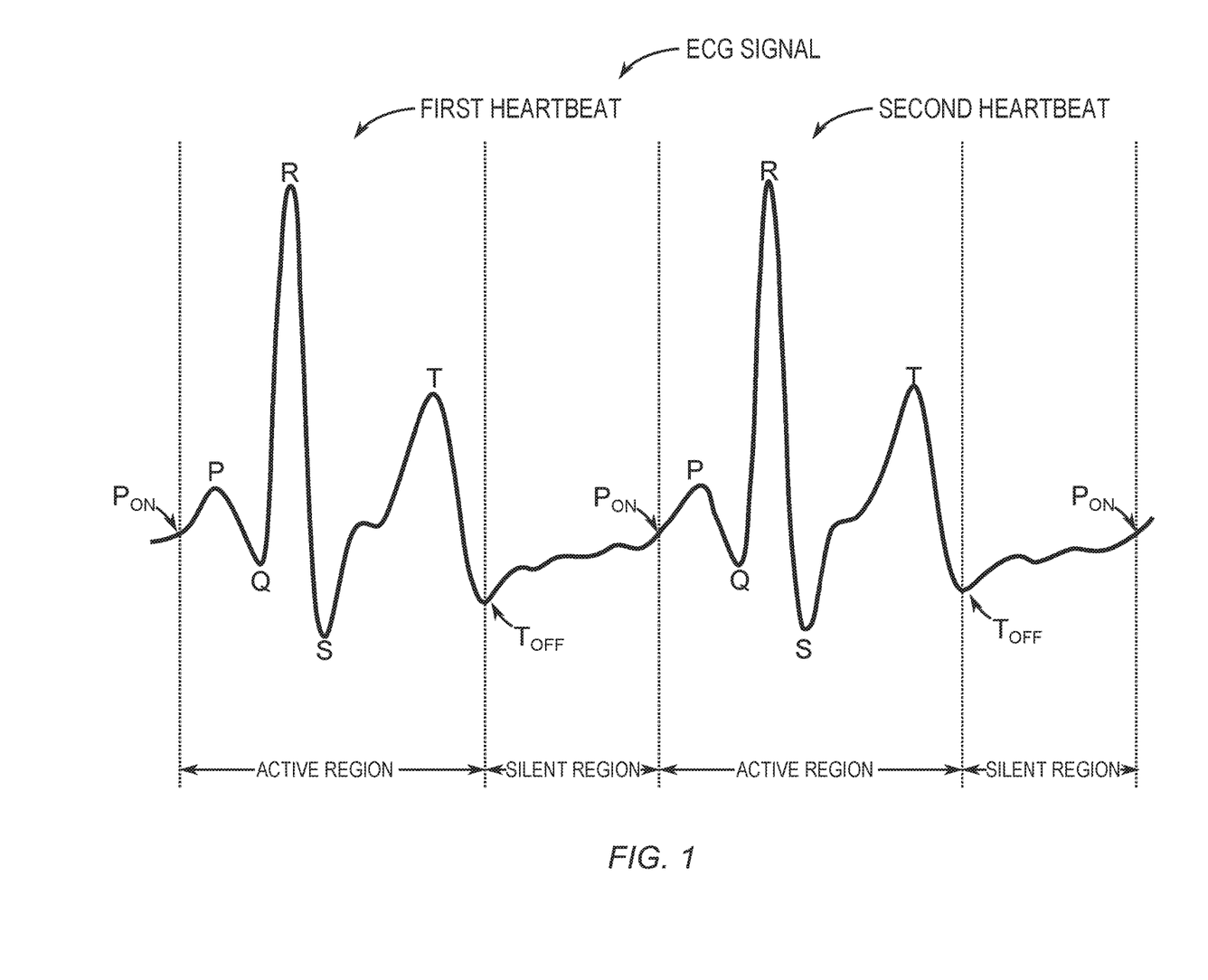
FIG. 1 is a depiction of an electrocardiogram (ECG) signal that is processed in accordance with the present disclosure.

FIG. 1 is a depiction of an exemplary electrocardiogram (ECG) signal that is processed in accordance with the present disclosure. The ECG signal is an electrical signal having voltage modulation that indicates a first heartbeat and a second heartbeat. As shown in FIG. 1, the ECG signal is divided into active regions and silent regions. Information of interest about the first heartbeat and second heartbeat indicated by the ECG signal is contained within the active regions. The silent regions are not completely silent in an electrical sense, but the silent regions typically do not contain information of interest. Therefore, the present disclosure treats the silent regions as if they were completely silent from an ECG diagnostics point of view.

The information of interest within the active regions are onset of the P-wave $P_{ON}$, the P-wave, the Q peak, the R peak, the S peak, the T-wave, and the end of the T-wave $T_{OFF}$. The onset of the P-wave $P_{ON}$, the Q peak, the R peak, the S peak, and the end of the T-wave $T_{OFF}$ make up a PQRST complex. To capture the information of interest, a portion of the ECG signal within the active region is sampled. In accordance with the present disclosure, active regions are defined to be between the onset of the P-wave $P_{ON}$ and the end of the T-wave $T_{OFF}$ of an individual heartbeat such as the first heartbeat and the second heartbeat. Also, in accordance with the present disclosure, silent regions are defined to be between the end of the T-wave $T_{OFF}$ of a proceeding heartbeat such as the first heartbeat and the beginning of the P-wave $P_{ON}$ of a next heartbeat such as the second heartbeat.

Restricting data acquisition, i.e., sampling of ECG signals to only the active regions of ECG signals reduces the number of bytes of a memory chip used to store digital samples of the ECG signal. Moreover, if the locations of the active regions are known, a compressive sensing technique can be employed to further greatly reduce the number of bytes of a memory chip used to store digital samples of the ECG signal. However, accurately locating the active regions using compressive sensing is not reliable. Therefore, the present disclosure employs Nyquist rate sampling of the ECG signal for a first predetermined number of heartbeats to provide an average relative location of the active regions within the ECG signal. Once an average relative location of the active regions is determined, compressive sensing is employed to acquire a minimal number of ECG signal samples from the active regions that allows a faithful reproduction of the ECG signal using the minimal ECG signal samples. This combination of Nyquist sampling and compressive sensing provides a unique automated adaptive compressive sensing technique that provides compression ratios between Nyquist sampling and compressive sampling of at least 3.2:1, which is greater than compression ratios realized by employing compressive sensing alone.

Figure 2:
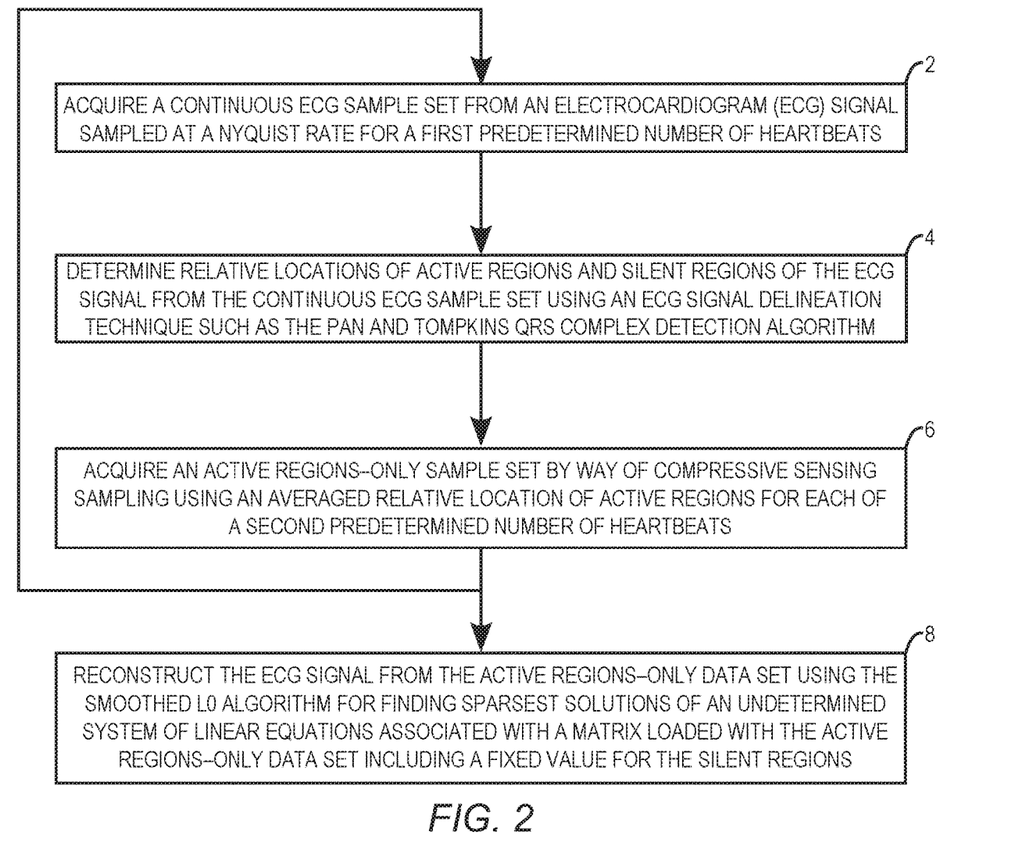
FIG. 2 is a flowchart for an automated adaptive compressive sensing technique that is implemented by an ECG processor of the present disclosure.

FIG. 2 is a flowchart for an automated adaptive compressive sensing technique that is implemented by an ECG processor of the present disclosure. ECG signal processing begins with acquiring a continuous ECG sample set from an ECG signal sampled at a Nyquist rate for a first predetermined number of heartbeats (step 2). In an exemplary embodiment, the first predetermined number of heartbeats is between three and five heartbeats. Next, the ECG processor determines relative locations of active regions and silent regions of the ECG signal from the continuous ECG sample set (step 4). The ECG processor may process the continuous ECG sample set using an ECG signal delineation technique such as the Pan and Tompkins QRS complex detection algorithm. Next, the ECG processor then acquires an active regions-only sample set by way of compressive sensing sampling using an average relative location of the active regions for each of a second predetermined number of heartbeats (step 6). The ECG processor determines the average relative location of the active regions by averaging the active region located in step 5. In some embodiments, the second predetermined number of heartbeats is between 8 and 16 heartbeats. The ECG processor then repeats steps 2-6 until a desired number of heartbeats have been processed. At that point, the ECG processor may reconstruct the ECG signal from the active regions-only sample set using the smoothed L0 algorithm for finding the sparsest solutions of an undetermined system of linear equations associated with a matrix loaded with the active regions-only sample set including a fixed value for the silent regions (step 8).

Figure 3:
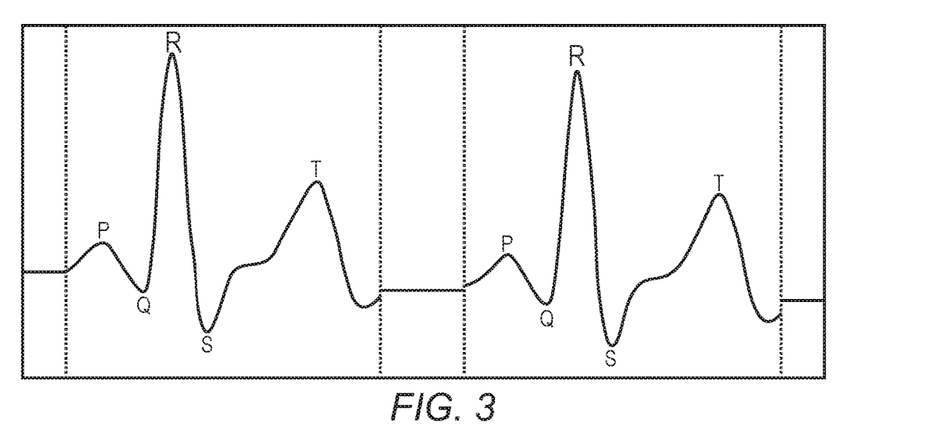
FIG. 3 is a depiction of an ECG signal reconstructed from an active regions-only sample set acquired by way of the automated adaptive compressive sensing technique in accordance with the present disclosure.

FIG. 3 is a depiction of an ECG signal reconstructed from an active regions-only sample set acquired by way of the automated adaptive compressive sensing technique of FIG. 2. The reconstructed ECG signal of FIG. 3 shows that the ECG processor provides fixed sample values for reconstructed silent regions. In some embodiments, the fixed sample value is equal to the last sample value of a previously reconstructed active region.

Figure 4:
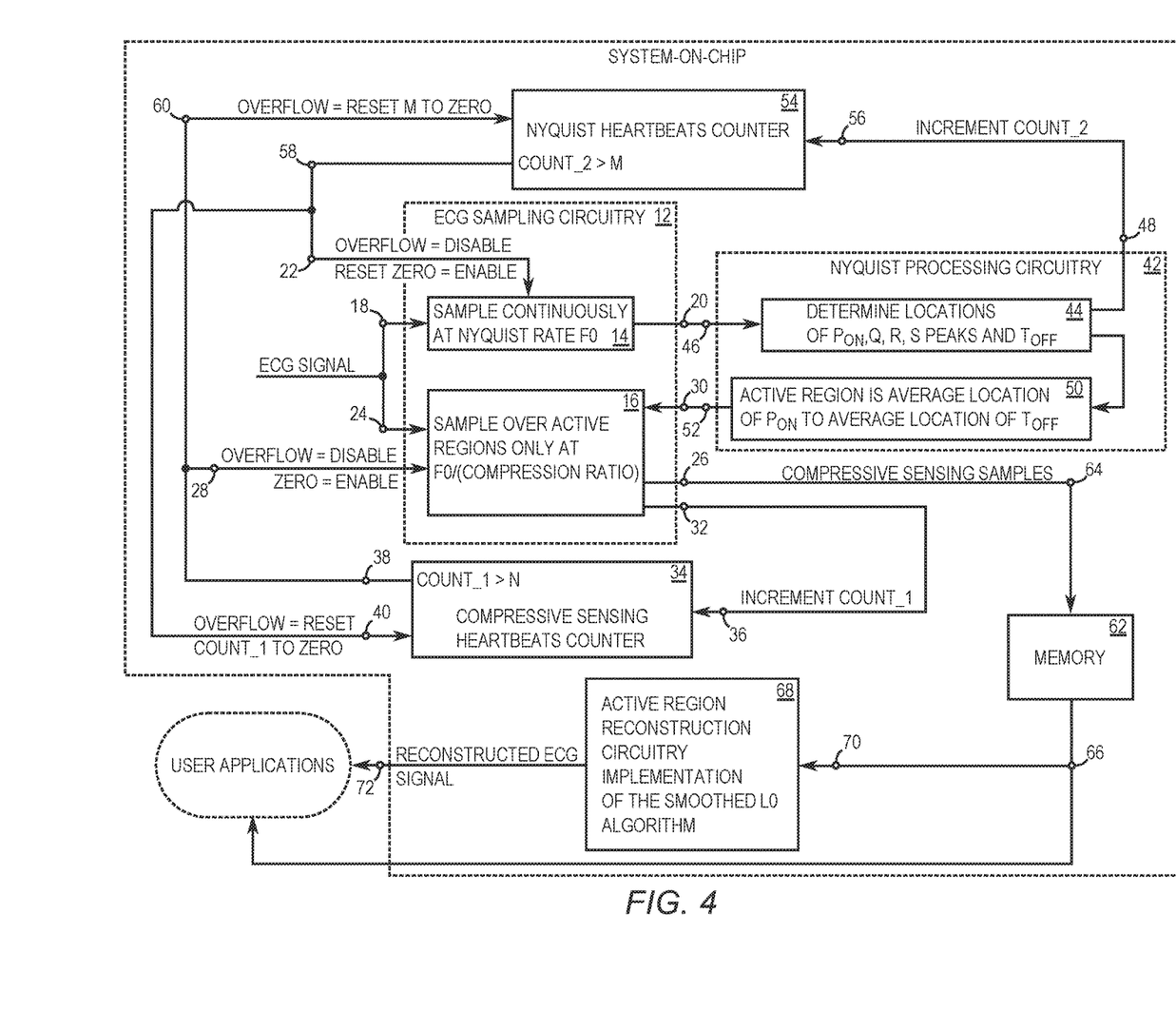
FIG. 4 is a depiction of a system-on-chip (SOC) embodiment of the ECG processor that provides automatic adaptive compressive sensing of an ECG signal in accordance with the present disclosure.

FIG. 4 is an embodiment of an ECG processor in the form of a system-on-chip (SOC) 10 that provides automatic adaptive compressive sensing of an ECG signal in accordance with the present disclosure. The SOC 10 may be implemented with technologies such as field-programmable gate arrays, application-specific integrated circuits, digital signal processors, and combinations thereof.

The SOC 10 includes electronic digital logic gates and may include electronic amplifiers with active and passive filtering. In particular, the SOC 10 has ECG sampling circuitry 12 that includes a Nyquist rate sampler 14 and a compressive sensing sampler 16. In exemplary embodiments, the Nyquist rate sampler 14 has an analog-to-digital converter configured to sample the ECG signal at a Nyquist rate F0. A typical Nyquist rate F0 for sampling an ECG signal is 250 Hz.

The Nyquist rate sampler 14 has a first analog input 18 through which the ECG signal is received. The Nyquist rate sampler 14 further includes a first digital output 20 through which digitized samples of the ECG signal are provided for further processing. The Nyquist rate sampler 14 also includes a first control input 22 that enables and disables Nyquist rate sampling of the ECG signal. In exemplary embodiments, the first control input 22 receives binary logic signals such as a logic one and a logic zero. An example of a logic one may be a predefined voltage level such as 1 V and an example of a logic zero may be a predefined voltage level such as 0 V. The Nyquist rate sampler 14 is responsive to binary logic signals used to enable and disable the Nyquist sampling of the ECG signal arriving at the first analog input 18. For example, an enable signal such as a logic one arriving at the first control input 22 causes the Nyquist rate sampler 14 to provide digitized samples of the ECG signal through the first digital output 20. A disable signal such as a logic zero arriving at the first control input 22 causes the Nyquist rate sampler 14 to stop providing digitized samples of the ECG signal through the first digital output 20. In exemplary embodiments, the Nyquist rate sampler 14 is placed in a first low power mode when a disable signal arrives at the first control input 22.

In exemplary embodiments, the compressive sensing sampler 16 has an analog-to-digital converter that samples predetermined portions of the ECG signal at a fraction of the Nyquist rate F0. However, it is to be understood that in some embodiments, the analog-to-digital converter of the compressive sensing sampler 16 is the same analog-to-digital converter of the Nyquist rate sampler 14. In such embodiments, at least one of the control signals that enables and disables either of the Nyquist rate sampler 14 or the compressive sensing sampler 16 may also set a sample rate of the analog-to-digital converter.

In other exemplary embodiments, the Nyquist rate sampler 14 and the compressive sensing sampler 16 may each have dedicated analog-to-digital converters with fixed sampling rates. For example, the Nyquist rate sampler 14 may have a first dedicated analog-to-digital converter having a sampling rate fixed at the Nyquist rate F0, and the compressive sensing sampler 16 may have a second analog-to-digital converter with a slower sampling rate fixed at a fraction of the Nyquist sampling rate F0. In exemplary embodiments, the fraction of the Nyquist rate F0 is equal to F0 divided by a compression ratio. An exemplary compression ratio in accordance with the present disclosure is 3.2:1. Thus, in an exemplary embodiment, a compressive sensing sampling rate is 250 Hz/3.2 or 78 Hz.

The compressive sensing sampler 16 has a second analog input 24 through which the ECG signal is received. The compressive sensing sampler 16 further includes a second digital output 26 through which compressive sensing samples of the active region of the ECG signal are provided. The compressive sensing sampler 16 also includes a second control input 28 that enables and disables the compressive sensing sampling rate of the ECG signal. In exemplary embodiments, the first control input 22 receives binary logic signals such as a logic one and a logic zero. The compressive sensing sampler 16 is responsive to binary logic signals used to enable and disable the compressive sensing sampling of the ECG signal arriving at the second analog input 24. For example, an enable signal such as a logic one arriving at the second control input 28 causes the compressive sensing sampler 16 to provide digitized samples of the active region of the ECG signal through the second digital output 26. A disable signal such as a logic zero arriving at the second control input 28 causes the compressive sensing sampler 16 to stop providing digitized samples of the active region of the ECG signal through the second digital output 26. In exemplary embodiments, the compressive sensing sampler 16 is placed in the first low power mode when a disable signal arrives at the second control input 28.

The compressive sensing sampler 16 further includes a digital signal input 30 that receives a digital signal that provides an average location and duration of active regions of the ECG signal. The compressive sensing sampler 16 uses the average location and duration of the active regions to schedule a start time and stop time for each active region undergoing compressive sensing sampling. A silent region in which no samples are taken is defined as being between the stop time of a previous active region and the start time of a next active region. An exemplary start time is the average onset of a P-wave $P_{ON}$, and an exemplary stop time is the average end time of a T-wave $T_{OFF}$.

The compressive sensing sampler 16 may generate a first increment signal that indicates that the compressive sensing sampler 16 has encountered a new active region. The first increment signal is provided through a first increment output 32.

A compressive sensing heartbeats counter 34 is responsive to the first increment signal. A first increment input 36 is coupled to the first increment output 32 of the compressive sensing sampler 16. The compressive sensing heartbeats counter 34 includes a first count register COUNT_1 that is incremented by one for every active region that the compressive sensing sampler 16 encounters. The compressive sensing heartbeats counter 34 further includes a counter overflow output 38 that is coupled to the second control input 28 of the compressive sensing sampler 16. In operation, the compressive sensing heartbeats counter 34 generates an overflow signal when the first count register COUNT_1 overflows when the number of active regions encountered by the compressive sensing sampler 16 reaches a number greater than a predetermined number N. In an exemplary embodiment, the predetermined number N is set to between 8 and 16.

The overflow signal disables the compressive sensing sampler 16. A zero signal is generated by the compressive sensing heartbeats counter 34 when the first count register COUNT_1 is reset to zero. The zero signal is provided through the overflow output 38. The compressive sensing sampler 16 is enabled by the zero signal. The compressive sensing heartbeats counter 34 also includes a reset zero input 40 that receives a reset zero signal that resets the first count register COUNT_1 to zero.

Nyquist processing circuitry 42 has an ECG peaks locator 44 that determines locations of onset of the P-wave $P_{ON}$, the P-wave, the Q peak, the R peak, the S peak, the T-wave and the end of the T-wave $T_{OFF}$. The ECG peaks locator 44 has a Nyquist samples input 46 that is coupled to first digital output 20 of the Nyquist rate sampler 14. The ECG peaks locator 44 receives a continuous ECG sample set through the Nyquist samples input 46. In an exemplary embodiment, the ECG peaks locator 44 processes the continuous ECG sample set using the Pan and Tompkins QRS complex detection algorithm. In other words, the Nyquist processing circuitry 42 determines the relative locations of the active regions by implementing a Pan and Tompkins QRS complex search through the continuous ECG sample set. The ECG peaks locator 44 may generate a second increment signal each time the ECG peaks locator 44 locates a QRS complex associated with a heartbeat. The second increment signal is provided through a second increment output 48.

The Nyquist processing circuitry 42 further includes an active regions definer 50 that defines boundaries of the active regions. The active regions definer 50 receives locations of peaks located by the ECG peaks locator 44 and determines an average location of the onset of the P-wave $P_{ON}$ and an average location of the end of the T-wave $T_{OFF}$. The active region is defined as the average location of the onset of the P-wave $P_{ON}$ to the average location of the end of the T-wave $T_{OFF}$. These defined boundaries of the average active region are passed to the compressive sensing sampler 16 though a boundaries output 52 that is coupled to the digital signal input 30.

A Nyquist heartbeats counter 54 has a second increment input 56 and is coupled to the second increment output 48 of the ECG peaks locator 44. The Nyquist heartbeats counter 54 is responsive to the second increment signal generated by the ECG peaks locator 44.

The Nyquist heartbeats counter 54 includes a second count register COUNT_2 that is incremented by one for every heartbeat that the ECG peaks locator 44 locates. For example, in this exemplary embodiment, the ECG peaks locator 44 generates second increment signal at an instant an R peak is located. The Nyquist heartbeats counter 54 further includes a second counter overflow output 58 that is coupled to both the first control input 22 of the Nyquist rate sampler 14 and the reset zero input 40. In operation, the Nyquist heartbeats counter 54 generates an overflow signal when the second count register COUNT_2 overflows when the number of heartbeats processed by the ECG peaks locator 44 reaches a number greater than a predetermined number M. In an exemplary embodiment, the predetermined number M is set to between 3 and 5. The Nyquist heartbeats counter 54 also includes a reset zero input 60 that receives the reset zero signal that resets the second count register COUNT_2 to zero.

The SOC 10 further includes a memory 62 for storing compressive sensing samples generated by the compressive sensing sampler 16. Examples of memory types suitable for the memory 62 include but are not limited to static random access memory (SRAM) and non-volatile memory such as flash memory. The memory 62 has a first digital input 64 that is coupled to the second digital output 26 of the compressive sensing sampler 16. In an exemplary embodiment, compressive sensing samples arriving at the first digital input 64 are automatically stored sequentially in memory locations within the memory 62. Compressive sensing samples stored within the memory 62 are retrieved by user applications through a memory output 66.

In an exemplary embodiment, the SOC 10 further includes an active region reconstruction circuitry 68 that is a hardware implementation of a reconstruction algorithm such as the smoothed L0 algorithm used to find the sparsest solutions of an undetermined system of linear equations associated with the compressive sensing samples. The active region reconstruction circuitry 68 has second digital input 70 that is coupled to the memory output 66. Digital data making up reconstructed ECG signals is available to user applications through a third digital output 72.

Figure 5:
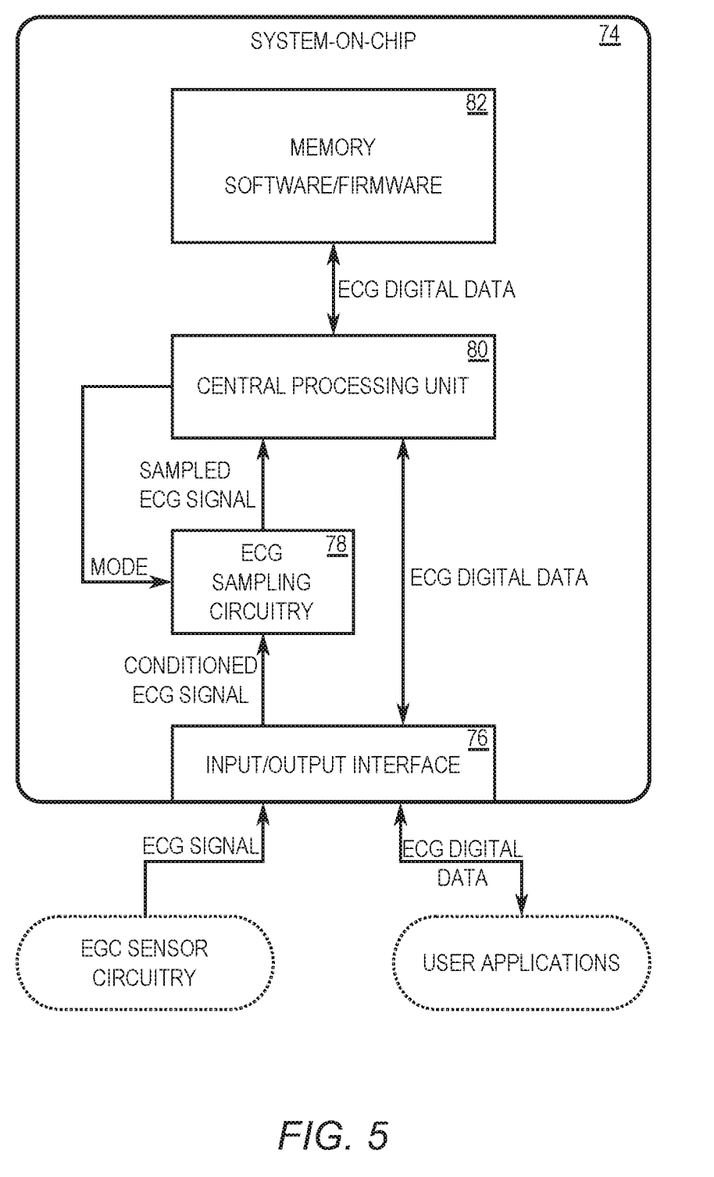
FIG. 5 is a depiction of an SOC that is an alternative embodiment of the ECG processor that provides automated adaptive compressive sensing of an ECG signal in accordance with the present disclosure.

FIG. 5 is a depiction of an SOC 74 that is an alternative embodiment of the ECG processor that provides automatic adaptive compressive sensing of the ECG signal in accordance with the present disclosure. The SOC 74 includes an input/output interface 76 for receiving an analog-type ECG signal from ECG sensor circuitry. The input/output interface 76 may amplify and filter the ECG signal in order to provide a conditioned ECG signal. It is to be understood from the exemplary embodiment of FIG. 5 that the input/output interface 76 is configured to interface with both digital signals and analog signals.

ECG sampling circuitry 78 receives and samples the conditioned ECG signal in two modes. In a first mode the ECG sampling circuitry 78 acquires a continuous ECG sample set from the conditioned ECG signal by digitally sampling the conditioned ECG signal at a Nyquist rate for a first predetermined number of heartbeats. In a second mode that performs a type of compressive sensing, the ECG sampling circuitry 78 acquires a non-continuous ECG sample set that is made up of compressive sensing samples.

In at least one exemplary embodiment, the first predetermined number of heartbeats is between three and five heartbeats and a second predetermined number of heartbeats is between 8 and 16 heartbeats. However, it is to be understood that the first predetermined number of heartbeats and the second number of predetermined heartbeats are selectable to higher or lower than the exemplary embodiment depending on changes in heart rate from lower to higher and vice versa. Moreover, the ECG sampling circuitry is configured to sample the active regions of the ECG signal that contain the PQRST complex in the second mode at a slower rate than the Nyquist rate. In exemplary embodiments, the slower rate is equal to the Nyquist rate divided by a compression ratio. In at least some exemplary embodiments, the compression ratio is between 2.6:1 and 3.2:1. As such, for a Nyquist rate of 250 Hz the slower rate is 78 Hz for a compression ratio of 3.2:1.

A central processing unit 80 controls the mode in which the ECG sampling circuitry operates, processes the sampled ECG signal, and directs ECG data flow. In order to provide appropriate mode control, the central processing unit 80 initially receives a portion of the sampled ECG signal from the ECG sampling circuitry 78 operating in the first mode that samples the conditioned ECG signal at the Nyquist rate for the first predetermined number of heartbeats to provide the central processing unit 80 with a continuous ECG sample set.

The central processing unit 80 then processes the continuous ECG sample set to determine relative locations of the active regions. In an exemplary embodiment, the central processing unit 80 processes the continuous ECG sample set using the Pan and Tompkins QRS complex detection algorithm. Once the relative locations of the active regions have been determined, the central processing unit indicates to the ECG sampling circuitry 78 the relative locations of the active regions and changes the mode of the ECG sampling circuitry 78 to the second mode that acquires the non-continuous ECG sample set from the ECG signal for the second predetermined number of heartbeats.

A memory 82 receives the non-continuous ECG sample set as digital ECG data that is stored within a data storage block of the memory 82. The memory 82 can be a non-volatile random access memory (NVRAM) such as flash memory, or the memory 82 can be static RAM (SRAM) or a combination of NVRAM and SRAM. In the latter case, instructions executed by the central processing unit 80 may be stored as firmware in the NVRAM and/or transferred from NVRAM to a block of program memory made up of SRAM. In at least some embodiments, the firmware may be updated through the input/output interface 76.

External applications may access the digital ECG data stored within the memory 82 for the digital ECG data by sending a request to the central processing unit 80 through the input/output interface 76. Upon receiving the request, the central processing unit 80 retrieves the digital ECG data and passes the ECG digital data through the input/output interface 76, which may provide level shifting and handshaking with devices that are controlled by the user applications.

Alternatively, the central processing unit 80 may reconstruct the active regions of the ECG signal by executing a reconstruction algorithm such as the smoothed L0 algorithm used to find the sparsest solutions of an undetermined system of linear equations associated with the compressive sensing samples of the non-continuous ECG sample set. In at least one exemplary embodiment, the central processing unit 80 generates a reconstructed ECG signal by processing the non-continuous ECG data using a smoothed L0 algorithm to reconstruct active regions and substitute fixed values for the silent regions between adjacent active regions.

An exemplary user application is a medical implantable wireless sensor node (WSN) application. The medical implantable WSN application takes advantage of the compression ratio of at least 3.2:1, a correlation coefficient of 98%, and a percentage root mean square difference of at least 7 that is provided by the performance of the exemplary embodiment of SOC 10 depicted in FIG. 4. In general, examples of user applications include but are not limited to battery-powered mobile health care devices having ECG sensors, pacemakers, and health-related Internet-of-Things (IoT) devices.

Those skilled in the art will recognize improvements and modifications to the preferred embodiments of the present disclosure. All such improvements and modifications are considered within the scope of the concepts disclosed herein and the claims that follow.

What is claimed is:

1. An electrocardiogram (ECG) processor comprising:
ECG sampling circuitry comprising an analog-to-digital converter, wherein the EGC sampling circuitry is configured in a first mode to acquire a continuous ECG sample set from an ECG signal by digitally sampling the ECG signal by way of the analog-to-digital converter at a Nyquist rate for a first predetermined number of heartbeats and in a second mode to acquire a non-continuous ECG sample set from the ECG signal for a second predetermined number of heartbeats by digitally sampling by way of the analog-to-digital converter active regions of the ECG signal that contain a PQRST complex and not from silent regions between adjacent PQRST complexes; and
processing circuitry configured to:
determine from the continuous ECG sample set relative locations of the active regions and provide the relative locations of the active regions to the ECG sampling circuitry for sampling the ECG signal in the second mode; and
generate a reconstructed ECG signal by processing the non-continuous ECG data using a smoothed L0 algorithm to reconstruct active regions and substitute fixed values for the silent regions between adjacent active regions.

2. The ECG processor of claim 1 further including a memory configured to store the non-continuous ECG sample set.

3. The ECG processor of claim 2 wherein the processing circuitry is a central processing unit (CPU).

4. The ECG processor of claim 3 wherein a memory is further configured to store CPU instructions that when executed by the CPU determine the relative locations of the active regions from the continuous ECG sample set.

5. The ECG processor of claim 4 wherein the CPU instructions are software.

6. The ECG processor of claim 5 wherein the CPU instructions are firmware.

7. The ECG processor of claim 1 wherein the ECG sampling circuitry is configured to sample the active regions of the ECG signal that contain the PQRST complex in the second mode at a slower rate than the Nyquist rate.

8. The ECG processor of claim 7 wherein the slower rate is equal to the Nyquist rate divided by a compression ratio.

9. The ECG processor of claim 8 wherein the compression ratio is between 2.6 and 3.2.

10. The ECG processor of claim 8 wherein the Nyquist rate is 250 Hz and the slower rate is 78 Hz.

11. The ECG processor of claim 1 wherein the processor circuitry determines the relative locations of the active regions by implementing a Pan and Tompkins QRS complex search through the continuous ECG sample set.

12. The ECG processor of claim 11 further configured to substitute fixed values for silent regions between adjacent reconstructed active regions to generate the reconstructed ECG signal.

13. The ECG processor of claim 1 wherein the first predetermined number of heartbeats is between three and five heartbeats.

14. The ECG processor of claim 1 wherein the second predetermined number of heartbeats is between 8 and 16 heartbeats.

15. The ECG processor of claim 1 wherein the first predetermined number of heartbeats is between three and five heartbeats and the second predetermined number of heartbeats is between 8 and 16 heartbeats.

16. The ECG processor of claim 1 further configured to generate reconstructed active regions from the non-continuous ECG data set.

17. The ECG processor of claim 1 wherein the ECG processor is a system-on-chip (SOC).

18. The ECG processor of claim 17 wherein the SOC is at least partially implemented with field-programmable gate array technology.

19. The ECG processor of claim 17 wherein the SOC is implemented as an application-specific integrated circuit.

* * * * *

UNITED STATES PATENT AND TRADEMARK OFFICE
CERTIFICATE OF CORRECTION

PATENT NO.        : 11,051,747 B2
APPLICATION NO.   : 15/716964
DATED             : July 6, 2021
INVENTOR(S)       : Hamza Yacoub Al Maharmeh et al.

Page 1 of 1

It is certified that error appears in the above-identified patent and that said Letters Patent is hereby corrected as shown below:

On the Title Page

Item (54):
Replace "ELECTROCARDIAGRAM (ECG) PROCESSOR" with --ELECTROCARDIOGRAM (ECG) PROCESSOR--.

In the Specification

Column 1, Lines 1-2, replace "ELECTROCARDIAGRAM (ECG) PROCESSOR" with --ELECTROCARDIOGRAM (ECG) PROCESSOR--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*